United States Patent [19]

Tavs et al.

[11] Patent Number: 4,820,874
[45] Date of Patent: Apr. 11, 1989

[54] INCREASING THE YIELD OF 2.5.6-TRIMETHYLCYCLOHEX-2-EN-1-ONE

[75] Inventors: Peter Tavs, Limburgerhof; Harald Laas, Maxdorf; Horst Schauer, Mutterstadt; Lothar Arnold, Heidelberg, all of Fed. Rep. of Germany

[73] Assignee: BASF Aktiengesellschaft, Ludwigshafen, Fed. Rep. of Germany

[21] Appl. No.: 111,603

[22] Filed: Oct. 23, 1987

[30] Foreign Application Priority Data

Oct. 23, 1986 [DE] Fed. Rep. of Germany ....... 3636057

[51] Int. Cl.$^4$ .............................................. C07C 45/67
[52] U.S. Cl. ..................................... 568/350; 568/345
[58] Field of Search ......................... 568/341, 345, 350

[56] References Cited

U.S. PATENT DOCUMENTS 3,531,504  9/1970  Conia .................................... 568/341
3,857,892 12/1974  Wehrli ................................... 568/345
4,081,482  3/1978  Baumann et al. .................... 568/345
4,128,728 12/1978  Arnold et al. ........................ 568/345

Primary Examiner—James H. Reamer
Attorney, Agent, or Firm—Keil & Weinkauf

[57] ABSTRACT

The yield of 2,5,6-trimethyl-cyclohex-2-en-1-one is increased by reacting diethyl ketyone, in the presence of an alkali, with crotonaldehyde or a compound which is converted to crotonaldehyde under the reaction conditions chose, and working up the reaction mixture by distillation, by a method in which the distillation residue obtained is either (a) heated at from 120° to 250° C. in particular from 120° to 200° C., with the addition of a catalytic amount of an alkali, or (b) heated at from 150° to 250° C. without the addition of such a substance, and the mixture of 2,5,6-trimethylcyclohex-2-en-1-one and diethyl ketone which is formed from the distillation residue as a result of the heat treatment is separated by distillation.

8 Claims, No Drawings

INCREASING THE YIELD OF 2.5.6-TRIMETHYLCYCLOHEX-2-EN-1-ONE

The present invention relates to a process for increasing the yield of 2,5,6-trimethylcyclohex-2-en-1-one. The compound can be dehydrogenated to 2,3,6-trimethylphenol, which is an important intermediate for the synthesis of vitamin E.

DE-C-17 93 037 describes a process for the preparation of 2,5,6-trimethylcyclohex-2-en-1-one by reacting diethyl ketone, in the presence of an alkali, with crotonaldehyde or a compound which is converted to crotonaldehyde under the reaction conditions chosen, and working up the reaction mixture by distillation. However, the yields of the known process are unsatisfactory and, according to the Examples, are from 40 to 77%.

It is an object of the present invention to provide a process for increasing the yield of 2,5,6-trimethylcyclohex-2-en-1-one, the process having the features of the preamble of claim 1.

We have found that this object is achieved by a process of the type stated at the outset, wherein the distillation residue obtained is either (a) heated at from 120° to 250° C., in particular from 120° to 200° C., with the addition of a catalytic amount of an alkali, or (b) heated at from 150° to 250° C. without the addition of such a substance, and the mixture of 2,5,6-trimethylcyclohex-2-en-1-one and diethyl ketone which is formed from the distillation residue as a result of the heat treatment is separated by distillation.

In a preferred embodiment, from 0.5 to 5% by weight, based on the distillation residue, of potassium hydroxide solution is added.

In another preferred embodiment, the heat treatment is carried out under atmospheric pressure, and the diethyl ketone formed is distilled off under atmospheric pressure, after which the 2,5,6-trimethylcyclohex-2-en-1-one is distilled off under reduced pressure. Where distillation is carried out under reduced pressure, a range from 20 to 100 mbar is particularly advantageous.

In another preferred embodiment, the heat treatment is carried out under reduced pressure, the mixture of diethyl ketone and 2,5,6-trimethylcyclohex-2-en-1-one formed being distilled off under reduced pressure.

The cleavage of the distillation residue can be carried out either batchwise or continuously. In the continuous procedure, it is preferable to effect the heat treatment in a reaction column, the distillation residue being pumped to the lower part of the column or to the bottom, and the mixture of 2,5,6-trimethylcyclohex-2-en-1-one and diethyl ketone which is formed by the cleavage reaction in the bottom is taken off at the top of the column.

In a further preferred embodiment, the heat treatment may alternatively be carried out in a stirred kettle during a residence time of, in particular, from 0.5 to 3 hours, the diethy ketone and a small amount of 2,5,6-trimethylcyclohex-2-en-1-one distilling off, and the major part of the 2,5,6-trimethylcyclohex-2-en-1-one subsequently being separated from high boiling products in a distillation column.

If the cleavage is carried out at from 200° to 250° C., in particular above 220° C., it may be advantageous if from 5 to 20% by weight, based on the distillation residue, of an inert, high boiling mineral oil fraction is added to the distillation residue. This maintains the pumpability of the high boiling residue after the cleavage reaction. An example of a suitable mineral oil fraction is solvent oil.

In principle, it was to be expected that the novel heat treatment of the distillation residue would result in the latter becoming resinous or giving undesirable decomposition products. However, it was found, surprisingly, that the distillation residue contains a group of compounds having a molecular weight of 224, which undergo thermal or catalytic cleavage under the conditions according to the invention to give 2,5,6-trimethylcyclohex-2-en-1-one and diethyl ketone.

In the process according to the invention, from 120 to 180 kg of 2,5,6-trimethylcyclohex-2-en-1-one and from 85 to 110 kg of diethylketone can be obtained from one metric ton of distillation residue. The distillate obtained in the decomposition consists of from 82 to 91% of the stated useful products, which can then be separated by simple distillation.

In the novel process, diethyl ketone and crotonaldehyde are generally used as starting materials. However, instead of crotonaldehyde, it is also possible to use compounds which are converted to crotonaldehyde under suitable reaction conditions. Examples of these are β-hydroxybutyraldehyde and β-methoxybutraldehyde. In general, the diethyl ketone is used in excess. Working up by distillation gives, as a first fraction, the excess of the diethyl ketone used and, as a second fraction, the desired product. The distillation residue remains, and is worked up by the measures of the novel process. Alternatively, a higher boiling fraction can be taken off as a third fraction and then further processed according to the invention, in the same way as the distillation residue.

The Examples which follow illustrate the invention.

The distillation residue used in the Examples below is obtained as described in DE-C-17 93 037.

EXAMPLE 1

Cleavage with potassium hydroxide solution 1200 g of the distillation residue and 15 g of 50% strength potassium hydroxide solution are introduced into a distillation apparatus. The apparatus is evacuated (about 20 mmHg), and the mixture is heated from 70° C. to 175° C. in the course of 75 minutes. The distillation receiver is cooled with ice water. 136 g of virtually colorless product distills. According to analysis by gas chromatography, the distillate contains 70.5 g of 2,5,6-trimethylcyclohex-2-en-1-one (TMCH) and 42.2 g of diethyl ketone (DEK).

Decomposition of distillation residue of TMCH with potassium hydroxide solution (experimental conditions as above)

| Distillation residue g | 50% KOH g | Distillate TMCH g | DEK g |
| --- | --- | --- | --- |
| 1200 | — | 68.2 | 36.9 |
| 1200 | 15 | 70.3 | 42.1 |
| 1200 | 30 | 126.7 | 66.7 |
| 1200 | 60 | 174.9 | 103.9 |

EXAMPLE 2

Cleavage with potassium hydroxide solution under atmospheric pressure, distillation under reduced pressure 418 kg of distillation residue and 21 kg of 50% strength KOH are introduced into an 800 l stirred kettle. The kettle content is heated to 170° C. under atmospheric pressure and kept at this temperature for 2 hours. A total of 44.9 kg of product distill over, the product separating into two layers. The lower phase consists of 12 kg of water, which is separated off. The pressure is then reduced, and a total of 82.1 kg of distillate are obtained, under 45 mmHg in the final stage. A total of 115 kg of organic product is obtained. This contains 65.13 kg of TMCH and 37.84 kg of DEK, according to analysis by gas chromatography.

EXAMPLE 3

Cleavage without potassium hydroxide solution 500 g of distillation residue are heated at 248° C. (oil bath) in a distillation apparatus on which a column (40×2.5 cm) is mounted. DEK and a little TMCH initially distill off. After 70 minutes, the bottom temperature is reduced to 160° C., and the TMCH formed is forced over by gradually evacuating the distillation apparatus.

A total of 158.1 g of colorless liquid is obtained which, according to analysis by gas chromatography, contains 85.7 g of TMCH and 50.2 g of DEK. After cooling, the distillation residue is viscous.

EXAMPLE 4

Example 3 is repeated with the addition of 50 g of solvent oil. 156.9 g of distillate, containing 86.0 g of TMCH and 47.4 g of DEK, are collected. After cooling, the distillation residue of this experiment has a low viscosity.

We claim:

1. In a process for producing 2,5,6-trimethylcyclohex-2-en-1-one by reacting diethyl ketone, in the presence of an alkali, with crotonaldehyde or a compound which is converted to crotonaldehyde and distilling the reaction mixture to recover the 2,5,6-trimethylcyclohex-2-en-1-one formed, wherein a distillation residue is also obtained in the reaction which contains compounds having a molecular weight of 224, the improvement which comprises: converting said compounds having a molecular weight of 224 into a mixture of additional 2,5,6-trimethylcyclo-hex-2-en-1-one and diethyl ketone by (a) heating the distillation residue at from 120° to 250° C. with the addition of a catalytic amount of an alkali, or (b) heating the distillation residue at from 150° to 250° C. without the addition of said alkali, and separating said mixture by distillation.

2. The process of claim 1, wherein the heat treatment takes place in the presence of a catalytic amount of an alkali at a temperature of from 120° to 200° C.

3. The process of claim 1, wherein from 0.5 to 5% by weight, based on the distillation residue, of potassium hydroxide solution is added during the heat treatment.

4. The process of claim 1, wherein the heat treatment is carried out under atmospheric pressure, the diethyl ketone formed is distilled off under atmospheric pressure and the 2,5,6-trimethylcyclohex-2-en-1-one is distilled off under reduced pressure.

5. The process of claim 1, wherein the heat treatment is carried out under reduced pressure and at the same time the resulting mixture of diethyl ketone and 2,5,6-trimethylcyclohex-2-en-1-one is distilled off under reduced pressure.

6. The process of claim 1, wherein the heat treatment is carried out continuously in a reaction column, the distillation residue being pumped to the lower part of the column or to the bottom, and the mixture of 2,5,6-trimethylcyclohex-2-en-1-one and diethyl ketone which is formed by the cleavage reaction in the bottom being taken off at the top of the column.

7. The process of claim 1, wherein the heat treatment is carried out in a stirred kettle during a residence time of from 0.5 to 3 hours, and subsequently the 2,5,6-trimethylcyclohex-2-en-1-one is separated from higher boiling products in a distillation column.

8. The process of claim 1, wherein heat treatment is carried out at from 200° to 250° C., from 5 to 20% by weight, based on the distillation residue, of an inert, high boiling mineral oil fraction being added to the distillation residue.

* * * * *